United States Patent
Dubief et al.

(10) Patent No.: US 6,432,908 B1
(45) Date of Patent: Aug. 13, 2002

(54) DETERGENT COSMETIC COMPOSITION COMPRISING AN AMPHOTERIC POLYMER CONTAINING FATTY CHAINS AND AN ESTER, AND USE THEREOF

(75) Inventors: Claude Dubief, Les Chesnay; Serge Restle, Saint-Prix, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/599,991

(22) Filed: Jun. 23, 2000

(30) Foreign Application Priority Data

Jun. 25, 1999 (FR) .............................. 99 08175

(51) Int. Cl.⁷ ............................................... C11D 3/37
(52) U.S. Cl. ..................... 510/476; 510/119; 510/130
(58) Field of Search ................................. 510/476, 119, 510/130

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 4,217,914 A | 8/1980 | Jacquet et al. | |
| 4,240,450 A | 12/1980 | Grollier et al. | |
| 4,402,977 A | 9/1983 | Grollier et al. | |
| 4,839,166 A | 6/1989 | Grollier et al. | |
| 4,923,695 A | * 5/1990 | Nowak, Jr. et al. | ........... 424/71 |
| 4,996,059 A | 2/1991 | Grollier et al. | |
| 5,089,252 A | 2/1992 | Grollier et al. | |
| 5,523,369 A | * 6/1996 | Liu et al. | ..................... 526/264 |

FOREIGN PATENT DOCUMENTS

| | | |
|---|---|---|
| DE | 44 04 493 | 1/1995 |
| EP | 0 337 354 | 10/1989 |
| FR | 2 270 846 | 12/1975 |
| FR | 2 383 660 | 10/1978 |
| FR | 2 470 596 | 6/1981 |
| FR | 2 519 863 | 7/1983 |
| FR | 2 598 611 | 11/1987 |
| WO | WO 98/44012 | 10/1998 |

OTHER PUBLICATIONS

International Cosmetic Ingredient Dictionary and Handbook, 7th ed., 1997, p. 684, 1997.*
M.R. Porter, "Handbook of Surfactants", Blackie & Son Ltd., Glasgow & London, 1991, pp. 116–178.
English language Derwent Abstract of DE 44 04 493. No date.

* cited by examiner

Primary Examiner—John Hardee
(74) Attorney, Agent, or Firm—Finnegan Henderson Farabow Garrett & Dunner, L.L.P.

(57) ABSTRACT

Detergent compositions containing, in a cosmetically acceptable medium, a washing base, at least one water-insoluble carboxylic acid ester and at least one amphoteric polymer comprising at least one monomeric unit chosen from (meth)acrylate and (meth)acrylamide types containing at least one fatty chain, the fatty chain containing from 8 to 30 carbon atoms. These compositions can have improved cosmetic properties, in particular in terms of smoothing the hair. The composition can be used for cleansing, caring for and styling the hair.

27 Claims, No Drawings

DETERGENT COSMETIC COMPOSITION COMPRISING AN AMPHOTERIC POLYMER CONTAINING FATTY CHAINS AND AN ESTER, AND USE THEREOF

The present invention relates to cosmetic compositions with improved properties which are intended simultaneously for cleansing and conditioning, and which comprise, in a cosmetically acceptable support, a washing base comprising surfactants with detergent power in which are also present carboxylic acid esters in combination with at least one amphoteric polymer comprising at least one monomeric unit chosen from (meth)acrylate and (meth)acrylamide types containing at least one fatty chain, the fatty chain containing from 8 to 30 carbon atoms.

The invention also relates to the use of the compositions in the above-mentioned cosmetic application.

It is common practice to use detergent hair compositions (or shampoos) based essentially on conventional surfactants of anionic, nonionic and/or amphoteric type in particular, but more particularly of anionic type, to cleanse and/or wash the hair. These compositions are applied on wet hair and the lather generated by massaging or rubbing with the hands allows, after rinsing with water, the removal of the various types of soiling initially present on the hair.

Admittedly, these base compositions have good washing power, but the intrinsic cosmetic properties associated with them nevertheless may remain very poor, in particular due to the fact that the relatively aggressive nature of such a cleansing treatment can result in the long run in more or less pronounced damage to the hair fiber which is associated in particular with the gradual removal of the lipids or proteins contained in or at the surface of the fiber.

Thus, to improve the cosmetic properties of the above detergent compositions, and more particularly of those which are known to be applied to sensitized hair (i.e., hair which has been damaged or embrittled, in particular under the chemical action of atmospheric agents and/or hair treatments such as permanent-waving, dyeing or bleaching operations), it is now common practice to introduce into these compositions additional cosmetic agents known as conditioners which are intended mainly to repair or limit the harmful or undesirable effects induced by the various treatments or aggressions which the hair fibers undergo or are exposed to more or less repeatedly. These conditioners can, of course, also improve the cosmetic behavior of natural hair.

The conditioners most commonly used to date in shampoos are silicones, which in fact can give washed, dry or wet hair markedly better ease of disentangling, softness and smoothness than that which can be obtained with the corresponding cleansing compositions from which they are absent.

However, and despite the progress recently made in the field of shampoos, these conditioners do not truly give complete satisfaction, such that there is currently still a strong need for products which have further improved performance qualities as regards one or more of the cosmetic properties mentioned above.

The present invention is directed towards satisfying such a need.

Thus, after considerable research conducted in this matter, the inventors have now found, entirely surprisingly and unexpectedly, that by introducing at least one amphoteric polymer comprising at least one monomeric unit chosen from (meth)acrylate and (meth)acrylamide types containing at least one fatty chain, the fatty chain containing from 8 to 30 carbon atoms, into detergent compositions, in particular hair compositions, containing carboxylic acid esters, it is possible to substantially and significantly improve the cosmetic properties associated with these compositions, while at the same time conserving their good intrinsic washing power.

Without wishing to limit the present invention to any theory, there would appear to be specific interactions and/or affinities between the carboxylic acid esters, the amphoteric polymers in accordance with the invention and the hair during rinsing, which promote a uniform, sizeable and long-lasting deposition of the carboxylic acid esters and amphoteric polymers at the surface of the hair. This qualitative and quantitative deposition probably is one of the causes of the improvement that can be observed in the final properties, such as the ease of styling, the hold, the liveliness or the body of the treated hair.

All these discoveries form the basis of the present invention.

Thus, according to the present invention, detergent compositions, in particular hair compositions, are now proposed, comprising, in a cosmetically acceptable medium, a washing base, at least one water-insoluble carboxylic acid ester and at least one amphoteric polymer comprising at least one monomeric unit chosen from (meth)acrylate and (meth)acrylamide types containing at least one fatty chain, the fatty chain containing from 8 to 30 carbon atoms.

A subject of the invention is also the cosmetic use of the above compositions for cleansing, conditioning and styling the hair.

However, other characteristics, aspects and advantages of the invention will emerge even more clearly on reading the description which follows as well as the concrete, but in no way limiting, examples intended to illustrate it.

A—Washing Base

The compositions in accordance with the invention comprise a washing base, which is generally aqueous.

The surfactant(s) forming the washing base can be chosen, alone or as mixtures, from any and all anionic, amphoteric, nonionic, zwitterionic or cationic surfactants. However, according to the invention, the washing base preferably comprises anionic surfactants or mixtures of anionic surfactants and amphoteric surfactants or nonionic surfactants.

The minimum amount of washing base is that which is just sufficient to give the final composition a satisfactory foaming and/or detergent power, and excessive amounts of washing base do not really provide any additional advantages.

Thus, according to the invention, the washing base can preferably represent from 4% to 50% by weight, more preferably from 6% to 25% by weight and even more preferably from 8% to 20% by weight, relative to the total weight of the final composition.

The surfactants which are suitable for carrying out the present invention are, in particular, the following:

(i) Anionic Surfactant(s)

As examples of anionic surfactants which can be used, alone or mixed, in the context of the present invention, mention may be made in particular (non-limiting list) of salts (in particular alkaline salts, especially sodium salts, ammonium salts, amine salts, amino alcohol salts or magnesium salts) of the following compounds: alkyl sulphates, alkyl ether sulphates, alkylamidoether sulphates, alkylarylpolyether sulphates, monoglyceride sulphates; alkylsulphonates, alkyl phosphates, alkylamide sulphonates, alkylaryl sulphonates, α-olefin sulphonates, paraffin sulphonates; $(C_6-C_{24})$alkyl sulphosuccinates; $(C_6-C_{24})$alkyl ether sulphosuccinates; $(C_6-C_{24})$alkylamide sulphosuccinates; $(C_6-C_{24})$alkyl sulphoacetates; $(C_6-C_{24})$acylsarcosinates; and $(C_6-C_{24})$acyl glutamates. Use may also be made of the carboxylic esters of $(C_6-C_{24})$-alkyl polyglycosides such as alkyl glucoside citrates, alkyl polyglycoside tartrates and alkyl polyglycoside sulphosuccinates; alkyl sulphosuccinamates; acylisethionates and N-acyltaurates. The alkyl or acyl radical of all these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic acid, stearic acid, coconut oil acid or hydrogenated coconut oil acid; acyl lactylates in which the acyl radical contains 8 to 20 carbon atoms. Use may also be made of alkyl D-galactosiduronic acids and their salts, polyoxyalkylenated $(C_6-C_{24})$ alkyl ether carboxylic acids, polyoxyalkylenated $(C_6-C_{24})$ alkylaryl ether carboxylic acids, polyoxyalkylenated $(C_6-C_{24})$ alkylamido ether carboxylic acids and their salts, in particular those comprising from 2 to 50 alkylene oxide groups, particularly ethylene oxide groups, and mixtures thereof.

Anionic surfactants comprising a carboxylic group are particularly preferred.

(ii) Nonionic Surfactant(s)

Nonionic surfactants are, themselves also, compounds that are well known per se (see in particular in this respect "Handbook of Surfactants" by M. R. Porter, published by Blackie & Son (Glasgow and London), 1991, pp. 116–178, the disclosure of which is hereby incorporated by reference), and in the context of the present invention, their nature is not of critical importance. Thus, they can be chosen in particular from (non-limiting list) polyethoxylated, polypropoxylated or polyglycerolated alcohols, alpha-diols, alkylphenols or fatty acids containing a fatty chain containing, for example, 8 to 18 carbon atoms. The number of ethylene oxide or propylene oxide groups preferably ranges in particular from 2 to 50 and the number of glycerol groups preferably ranges in particular from 2 to 30. Mention may also be made of copolymers of ethylene oxide and of propylene oxide, condensates of ethylene oxide and of propylene oxide with fatty alcohols; polyethoxylated fatty amides preferably containing from 2 to 30 mol of ethylene oxide, polyglycerolated fatty amides comprising on average 1 to 5 and in particular 1.5 to 4 glycerol groups; polyethoxylated fatty amines preferably containing 2 to 30 mol of ethylene oxide; oxyethylenated fatty acid esters of sorbitan containing from 2 to 30 mol of ethylene oxide; fatty acid esters of sucrose, fatty acid esters of polyethylene glycol, alkylpolyglycosides, N-alkylglucamine derivatives, amine oxides such as $(C_{10}-C_{14})$alkylamine oxides or N-acylaminopropylmorpholine oxides. It will be noted that the alkylpolyglycosides constitute nonionic surfactants that are particularly suitable in the context of the present invention.

(iii) Amphoteric or Zwitterionic Surfactant(s)

The amphoteric or zwitterionic surfactants, whose nature, in the context of the present invention, can be, in particular (non-limiting list), aliphatic secondary or tertiary amine derivatives, in which the aliphatic radical is a linear or branched chain containing 8 to 18 carbon atoms and containing at least one water-solubilizing anionic group (for example carboxylate, sulphonate, sulphate, phosphate or phosphonate). Mention may also be made of $(C_8-C_{20})$alkyl betaines, sulphobetaines, $(C_8-C_{20})$alkylamido$(C_1-C_6)$alkylbetaines or $(C_8-C_{20})$alkylamido$(C_1-C_6)$alkylsulphobetaines.

Among the amine derivatives which may be mentioned are the products sold under the name MIRANOL, as described in U.S. Pat. Nos. 2,528,378 and 2,781,354 and classified in the CTFA dictionary, 3rd Edition, 1982, the disclosures of which are hereby incorporated by reference, under the trade names Amphocarboxyglycinates and Amphocarboxypropionates, and of respective structures:

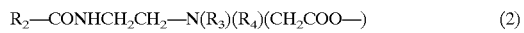

$$R_2\text{—CONHCH}_2\text{CH}_2\text{—N}(R_3)(R_4)(CH_2COO\text{—}) \quad (2)$$

in which: $R_2$ is an alkyl, preferably an alkyl radical of an acid $R_2$—COOH present in hydrolysed coconut oil, or a heptyl, nonyl or undecyl radical; $R_3$ is a beta-hydroxyethyl group; and $R_4$ is a carboxymethyl group; and

$$R_2'\text{—CONHCH}_2\text{CH}_2\text{—N(B)(C)} \quad (3)$$

in which:

B is —$CH_2CH_2OX'$, C is —$(CH_2)_z$—Y', with z being 1 or 2,

X' is an —$CH_2CH_2$—COOH group or a hydrogen atom,

Y' is —COOH or an —$CH_2$—CHOH—$SO_3H$ radical, $R_2'$ is an alkyl, preferably, an alkyl radical of an acid $R_2'$—COOH present in coconut oil or in hydrolysed linseed oil, or a $C_7$, $C_9$, $C_{11}$ or $C_{13}$ alkyl radical, or a $C_{17}$ alkyl radical and its iso form, or an unsaturated $C_{17}$ radical.

These compounds are classified in the CTFA dictionary, b 5th edition, 1993, the disclosure of which is hereby incorporated by reference, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid.

By way of example, mention may be made of cocoamphodiacetate sold under the trade name MIRANOL® C2M concentrate by the Company Rhodia Chimie.

In the compositions in accordance with the invention, mixtures of surfactants are preferably used, and in particular mixtures of anionic surfactants and amphoteric or nonionic surfactants. One mixture which is particularly preferred is a mixture comprising at least one anionic carboxylic surfactant and of at least one amphoteric or nonionic surfactant.

The anionic surfactant used is preferably chosen from polyoxyalkylenated $(C_6-C_{24})$alkyl ether carboxylic acids, polyoxyalkylenated $(C_6-C_{24})$alkylaryl ether carboxylic acids and polyoxyalkylenated $(C_6-C_{24})$alkylamido ether carboxylic acids and their mixture with a sulphone-containing or sulphate-containing surfactant such as sodium, triethanolamine or ammonium $(C_{12}-C_{14})$alkyl sulphates, sodium $(C_{12}-C_{14})$alkyl ether sulphates oxyethylenated with 2.2 mol of ethylene oxide, sodium cocoyl isethionate and mixtures thereof with:

either an amphoteric surfactant such as the amine derivatives known as disodium cocoamphodipropionate or sodium cocoamphopropionate sold in particular by the Company Rhodia Chimie under the trade name MIRANOL® C2M CONC as an aqueous solution containing 38% active material, or under the name MIRANOL® C32;

or an amphoteric surfactant of zwitterionic type such as alkylbetaines in particular the cocoylbetaine sold under the name DEHYTON® AB 30 as an aqueous solution containing 32% AM by the Company Henkel, or alkylamidoalkylbetaines such as TEGOBETAINE® F50 sold by the Company Goldschmidt;

or a nonionic surfactant of alkylpolyglucoside type.

(iv) Cationic Surfactants

Among the cationic surfactants which may be mentioned in particular (non-limiting list) are: optionally polyoxyalkylenated primary, secondary or tertiary fatty amine salts; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives or amine oxides of cationic nature.

It will be noted that cationic surfactants, the use of which is not excluded, do not constitute preferred surfactants for carrying out the present invention.

B—Esters

The compositions in accordance with the invention also comprise a carboxylic acid ester, the ester containing at least 10 carbon atoms.

The liquid water-insoluble carboxylic acid esters are insoluble in water at a concentration of greater than or equal to 0.1% by weight in water at 25° C., i.e., they do not form a transparent isotropic solution under these conditions.

The total number of carbon atoms in the esters is generally greater than or equal to 10 and preferably less than 100 and more particularly less than 80.

The acid esters can be mono-, di-, tri- or tetracarboxylic acid esters.

The monocarboxylic acid esters are, in particular, monoesters of saturated or unsaturated, linear or branched ($C_1$–$C_{26}$) aliphatic acids and of saturated or unsaturated, linear or branched ($C_1$–$C_{26}$) aliphatic alcohols, the total number of carbon atoms in the esters being greater than or equal to 10.

Among the monoesters which may be mentioned are dihydroabietyl behenate; octyldodecyl behenate; isocetyl behenate; cetyl lactate; ($C_{12}$–$C_{15}$)alkyl lactate; isostearyl lactate; lauryl lactate; linoleyl lactate; oleyl lactate; (iso) stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, and 2-hexyldecyl laurate.

Esters of ($C_4$–$C_{22}$) di- or tricarboxylic acids and of ($C_1$–$C_{22}$) alcohols and esters of mono-, di- or tricarboxylic acids and of ($C_2$–$C_{26}$) di-, tri-, tetra- or pentahydroxy alcohols can also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate dicaprate; tridecyl erucate; triisopropyl citrate; triisostearyl citrate; glyceryl trilactate; glyceryl trioctanoate; trioctyldodecyl citrate; and trioleyl citrate.

Among the esters mentioned above which are preferably used are ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate and isononyl isononanoate, and cetyl octanoate.

According to the invention, the carboxylic acid ester(s) can represent from 0.001% to 10% by weight, preferably from 0.005% to 5% by weight and even more preferably from 0.01% to 3% by weight, relative to the total weight of the final composition.

C—Amphoteric Polymers Comprising at Least One Fatty Chain

The detergent compositions, in particular hair compositions, in accordance with the invention, also contain at least one amphoteric polymer comprising at least one monomeric unit chosen from (meth)acrylate and (meth) acrylamide types containing at least one fatty chain, the fatty chain containing from 8 to 30 carbon atoms.

The amphoteric polymers according to the invention generally comprise from 1 to 20 mol % of the monomeric units containing a fatty chain, and preferably from 1.5 to 15 mol %, and even more particularly from 1.5 to 6 mol % relative to the total number of moles of monomeric units in the polymers.

The amphoteric polymers according to the invention can result from the copolymerization 1) of at least one monomer chosen from (meth)acrylate and (meth)acrylamide types of formula (Ia) and (Ib):

$$R_1-CH=C-\underset{O}{\overset{R_2}{\underset{|}{C}}}-Z-(C_nH_{2n})-\overset{R_3}{\underset{R_4}{\overset{|}{N^+}}}-R_5 \quad A^- \tag{Ia}$$

$$R_1-CH=C-\underset{O}{\overset{R_2}{\underset{|}{C}}}-Z-(C_nH_{2n})-N\overset{R_3}{\underset{R_4}{\diagdown}} \tag{Ib}$$

in which: $R_1$ and $R_2$, which may be identical or different, are a hydrogen atom or a methyl radical; $R_3$, $R_4$ and $R_5$, which may be identical or different, are chosen from linear and branched alkyl radicals containing from 1 to 30 carbon atoms;

Z is an NH group or an oxygen atom;

n is an integer ranging from 2 to 5; and $A^-$ is an anion derived from an organic or inorganic acid, such as a methyl sulphate anion or a halide such as chloride or bromide, 2) of at least one monomer chosen from (meth)acrylate and (meth)acrylamide types of formula (II)

$$R_6-CH=CR_7-COOH \tag{II}$$

in which: $R_6$ and $R_7$, which may be identical or different, are a hydrogen atom or a methyl radical; and 3) of at least one monomer chosen from (meth)acrylate and (meth)acrylamide types of formula (III):

$$R_6-CH=CR_7-COXR_8 \tag{III}$$

in which: $R_6$ and $R_7$, which may be identical or different, are a hydrogen atom or a methyl radical; X is an oxygen or nitrogen atom; and $R_8$ is chosen from linear and branched alkyl radical containing from 1 to 30 carbon atoms;

at least one of the (meth)acrylate and (meth)acrylamide type monomers of formula (Ia), (Ib) or (III) comprises at least one fatty chain containing from 8 to 30 carbon atoms.

The monomers of formulae (Ia) and (Ib) of the present invention are preferably chosen from:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate, and
dimethylaminopropylmethacrylamide, dimethylaminopropylacrylamide,
these monomers optionally being quaternized, for example with a ($C_1$–$C_4$) alkyl halide or a ($C_1$–$C_4$) dialkyl sulphate.

More particularly, the monomer of formula (Ia) is chosen from acrylamidopropyltrimethylammonium chloride and methacrylamidopropyltrimethylammonium chloride.

The monomers of formula (II) of the present invention are preferably chosen from acrylic acid, methacrylic acid, crotonic acid and 2-methylcrotonic acid.

The monomer of formula (II) is more particularly acrylic acid.

The monomers of formula (III) of the present invention are preferably chosen from ($C_{12}$–$C_{22}$) and more particularly ($C_{16}$–$C_{18}$) alkyl acrylates or methacrylates.

The monomers constituting the amphoteric polymers of the invention are preferably already neutralized and/or quaternized.

The ratio of the number of cationic charges/anionic charges is preferably equal to about 1.

The weight-average molecular weights of the amphoteric polymers according to the invention can range from 500 to 50,000,000 and preferably range from 10,000 to 5,000,000.

Polymers according to the invention can also contain other monomers such as nonionic monomers such as ($C_1$–$C_4$) alkyl acrylates or methacrylates.

Amphoteric polymers according to the invention are described, in particular, in patent application WO 98/44012, the disclosure of which is hereby incorporated by reference.

The amphoteric polymers that are particularly preferred according to the invention are chosen from acrylic acid/acrylamidopropyltrimethylammonium chloride/stearyl methacrylate copolymers.

The amphoteric polymer is preferably used in the composition in an amount ranging from 0.05 to 10% by weight relative to the total weight of the composition. This amount is more preferably from 0.1 to 5% by weight relative to the total weight of the composition.

The cosmetically acceptable aqueous medium can be solely water or a mixture of water and a cosmetically acceptable solvent such as a ($C_1$–$C_4$) lower alcohol, for instance ethanol, isopropanol, tert-butanol or n-butanol; alkylene glycols such as propylene glycol, and glycol ethers.

The composition preferably comprises from 50 to 95% by weight of water relative to the total weight of the composition.

The detergent compositions according to the invention have a final pH generally ranging from 3 to 10. This pH preferably ranges from 4 to 9. The pH can be adjusted to the desired value conventionally by adding a base (organic or inorganic) to the composition, for example aqueous ammonia or a primary, secondary or tertiary (poly)amine such as monoethanolamine, diethanolamine, triethanolamine, isopropanolamine or 1,3-propanediamine, or alternatively by adding an inorganic or organic acid, preferably a carboxylic acid such as, for example, citric acid.

The compositions in accordance with the invention can contain, in addition to the combination defined above, viscosity regulators such as electrolytes, or thickeners. Mention may be made in particular of sodium chloride, sodium xylene sulphonate, scleroglucans, xanthan gums, fatty acid alkanolamides, alkyl ether carboxylic acid alkanolamides optionally oxyethylenated with up to 5 mol of ethylene oxide, such as the product sold under the name AMINOL A15 by the Company Chem Y, crosslinked polyacrylic acids and crosslinked acrylic acid/($C_{10}$–$C_{30}$) alkyl acrylate copolymers. These viscosity regulators are used in the compositions according to the invention in proportions which may be up to 10% by weight relative to the total weight of the composition.

The compositions in accordance with the invention can also contain up to 5% of nacreous agents or opacifiers that are well known in the prior art, such as, for example, ($C_{16}$) higher fatty alcohols, sodium or magnesium palmitates, sodium or magnesium stearates and hydroxystearates, acyl derivatives containing a fatty chain, such as ethylene glycol or polyethylene glycol monostearates or distearates, and ethers containing fatty chains such as, for example, distearyl ether or 1-(hexadecyloxy)-2-octadecanol.

Needless to say, the detergent compositions according to the invention can also contain any common adjuvant encountered in the field of shampoos, such as, for example, fragrances, preserving agents, sequestering agents, thickeners, softeners, foam modifiers, dyes, nacreous agents, moisturizers, antidandruff agents, anti-seborrhoeic agents, sunscreens and the like.

The compositions in accordance with the invention can also optionally contain other agents whose effect is to improve the cosmetic properties of hair or skin without, however, adversely affecting the stability of the compositions. Mention may be made in this respect of anionic or nonionic polymers and more particularly cationic polymers, amphoteric polymers other than those of the invention, proteins, protein hydrolysates, ceramides, pseudoceramides, fatty acids containing linear or branched ($C_{16}$–$C_{40}$) chains such as 18-methyleicosanoic acid, hydroxy acids, vitamins, panthenol, volatile silicones, non-volatile silicones which may be soluble or insoluble in the medium, plant oils and synthetic oils, and mixtures thereof.

The compositions according to the invention preferably comprise one or more cationic polymers.

The cationic polymers which can be used in accordance with the present invention can be chosen from any of those already known per se as improving the cosmetic properties of hair treated with detergent compositions, i.e., in particular those described in patent application EP-A-0 337 354 and in French patent applications FR-A-2 270 846, 2 383 660, 2 598 611, 2 470 596 and 2 519 863, the disclosures of all of which are hereby incorporated by reference.

Even more generally, for the purposes of the present invention, the expression "cationic polymer" denotes any polymer containing cationic groups and/or groups which can be ionized into cationic groups.

Among the cationic polymers which can be used in the context of the present invention, the ones preferably used are quaternary cellulose ether derivatives such as the products sold under the name JR 400 by the company Union Carbide Corporation, cyclopolymers, in particular homopolymers of diallyldimethylammonium salt and copolymers of diallyldimethylammonium salt and of acrylamide, in particular the chlorides, sold under the names MERQUAT 100, MERQUAT 550 and MERQUAT S by the company Merck, cationic polysaccharides and more particularly guar gums modified with 2,3-epoxypropyltrimethylammonium chloride, which is sold, for example, under the name JAGUAR C13S by the Company Meyhall, vinylpyrrolidone/methacrylamidopropyldimethylamine copolymers, and mixtures thereof.

According to the invention, the cationic polymer(s) can represent from 0.001% to 10% by weight, preferably from 0.005% to 5% by weight and even more preferably from 0.01% to 3% by weight, relative to the total weight of the final composition.

The compositions according to the invention can also contain foam synergists such as ($C_{10}$–$C_{18}$) 1,2-alkanediols or fatty alkanolamides derived from monoethanolamine or from diethanolamine.

Needless to say, a person skilled in the art will take care to select this or these optional additional compound(s) and/or the amounts thereof such that the advantageous properties intrinsically associated with the combination in accordance with the invention are not, or are not substantially, adversely affected by the addition(s) envisaged.

These compositions can be in the form of more or less thickened liquids, creams or gels and are mainly suitable for washing, caring for and/or styling the hair.

The compositions of the invention can also be in the form of washing compositions for the skin, and in particular in the form of bath or shower solutions or gels or make-up-removing products.

When the compositions in accordance with the invention are used as conventional shampoos, they are simply applied to the keratin substances, in particular dry hair or, preferably, wet hair, and the lather generated by massaging or rubbing with the hands is then removed, after optionally leaving it to stand on the hair for a certain amount of time, by rinsing, preferably with water, it being possible for the operation to be repeated one or more times.

A subject of the invention is also a process for washing and conditioning keratin substances, which comprises applying to the dry or wet substances an effective amount of a composition as defined above, and then in rinsing them with water after optionally leaving the composition to stand on them for a certain amount of time.

A concrete but in no way limiting example intended to illustrate the invention will now be given.

EXAMPLE 1

A shampoo composition in accordance with the invention was prepared by mixing together the following compounds:

| | |
|---|---|
| Sodium lauryl ether sulphate (2.2 EO) | 15 g AM |
| Cocoylbetaine as an aqueous 30% solution (DEHYTON AB 30 from Henkel) | 5 g AM |
| Isopropyl palmitate | 2 g |
| Terpolymer of methacrylamidopropyltrimethylammonium chloride, acrylic acid and stearyl methacrylate (49 mol %/49 mol %/2 mol %) | 0.4 g AM |
| Sodium chloride | 4 g |
| Preserving agent | q.s. |
| pH adjusted to 7 | 7 |
| Water q.s. | 100 g |

Hair treated with the shampoo according to the invention was soft, smooth and easy to disentangle.

What is claimed is:

1. A detergent composition comprising at least one washing base, at least one water-insoluble carboxylic acid ester and at least one amphoteric polymer comprising at least one monomeric unit chosen from (meth)acrylate and (meth)acrylamide types containing at least one fatty chain, the fatty chain containing from 8 to 30 carbon atoms,
   wherein the at least one amphoteric polymer results from copolymerization
   1) of at least one monomer chosen from (meth)acrylate and (meth)acrylamide types of formula (Ia) and (Ib):

$$R_1-CH=C(R_2)-C(=O)-Z-(C_nH_{2n})-N^+(R_3)(R_4)-R_5 \quad A^- \quad \text{(Ia)}$$

$$R_1-CH=C(R_2)-C(=O)-Z-(C_nH_{2n})-N(R_3)(R_4) \quad \text{(Ib)}$$

in which:
   $R_1$ and $R_2$, which may be identical or different, are a hydrogen atom or a methyl radical; $R_3$, $R_4$ and $R_5$, which may be identical or different, are chosen from linear and branched alkyl radicals containing form 1 to 30 carbon atoms:
   Z is an NH group;
   n is an integer ranging from 2 to 5; and
   A is an anion derived from an organic or inorganic acid,
   2) of at least one monomer chosen from (meth)acrylate and (meth)acrylamide types of formula (II)

$$R_6-CH=CR_7-COOH \quad \text{(II)}$$

in which: $R_6$ and $R_7$, which may be identical or different, are a hydrogen atom or a methyl radical; and
   3) of at least one monomer chosen from (meth)acrylate and (meth)acrylamide types of formula (III):

$$R_6-CH=CR_7-COXR_8 \quad \text{(III)}$$

in which: $R_6$ and $R_7$, which may be identical or different, are a hydrogen atom or a methyl radical: X is an oxygen atom; and $R_8$ is chosen from linear and branched alkyl radicals containing from 1 to 30 carbon atoms;
   wherein at least one of the (meth)acrylate and (meth)acrylamide type monomers of formula (Ia), (Ib) or (III) comprise at least one fatty chain containing from 8 to 30 carbon atoms.

2. The composition according to claim 1, wherein the composition further comprises a cosmetically acceptable medium.

3. The composition according to claim 2, wherein the composition also comprises at least one additive chosen from anionic polymers, nonionic polymers, amphoteric polymers differing from said at least one amphoteric polymer, proteins, protein hydrolysates, ceramides, pseudoceramides, fatty acids containing linear ($C_{16}$–$C_{40}$) chains, fatty acids containing branched ($C_{16}$–$C_{40}$) chains, hydroxy acids, vitamins, panthenol, volatile silicones, non-volatile silicones which are soluble in the medium and non-volatile silicones which are insoluble in the medium, plant oils, and synthetic oils.

4. The composition according to claim 3, wherein the at least one additive is chosen from cationic polymers.

5. The composition according to claim 4, wherein the cationic polymers are chosen from quaternary cellulose ether derivatives, cyclopolymers, cationic polysaccharides and vinylpyrrolidone/methacrylamidopropyldimethylamine copolymers.

6. The composition according to claim 3, wherein said at least one additive is 18-methyleicosanoic acid.

7. The composition according to claim 1, wherein the at least one washing base comprises at least one surfactant chosen from anionic, amphoteric, nonionic and zwitterionic surfactants.

8. The composition according to claim 1, wherein the at least one washing base is present in a weight content ranging from 4% to 50% relative to the total weight of the composition.

9. The composition according to claim 8, wherein the at least one washing base is present in a weight content ranging from 6% to 25% relative to the total weight of the composition.

10. The composition according to claim 1, wherein the at least one amphoteric polymer comprises from 1 to 20 mol % of monomeric units containing a fatty chain relative to the total number of moles of monomeric units in said at least one polymer.

11. The composition according to claim 10, wherein the at least one amphoteric polymer comprises from 1.5 to 15 mol % of monomeric units containing a fatty chain relative to the total number of moles of monomeric units in said at least one polymer.

12. The composition according to claim 11, wherein the at least one amphoteric polymer comprises from 1.5 to 6 mol % of monomeric units containing a fatty chain relative to the total number of moles of monomeric units in said at least one polymer.

13. The composition according to claim 1, wherein the at least one monomer of formulae (Ia) and (Ib) are chosen from:
   dimethylaminoethyl methacrylate, dimethylaminoethyl acrylate,
   diethylaminoethyl methacrylate, diethylaminoethyl acrylate,
   dimethylaminoproply methacrylate, dimethylaminopropyl acrylate, and
   dimethylaminoproplymethacrylamide, dimethylaminopropylacrylamide,
these monomers optionally being quaternized.

14. The composition according to claim 1, wherein the at least one monomer of formula (Ia) is chosen from acrylamidopropyltrimethylammonium chloride and methacrylamidopropyltrimethylammonium chloride.

15. The composition according to claim 1, wherein the at least one monomer of formula (II) is chosen from acrylic acid, methacrylic acid, crotonic acid and 2-methylcrotonic acid.

16. The composition according to claim 1, wherein the at least one monomer of formula (III) is chosen from ($C_{12}$–$C_{22}$) alkyl acrylates and methacrylates.

17. The composition according to claim 16, wherein the at least one monomer of formula (III) is chosen from ($C_{16}$–$C_{18}$) alkyl acrylates and methacrylates.

18. The composition according to claim 1, wherein the at least amphoteric polymer is chosen from acrylic acid/acrylamidopropyltrimethylammonium chloride/stearyl methacrylate copolymers.

19. The composition according to claim 1, wherein the at least one amphoteric polymer is present in the composition in an amount ranging from 0.05 to 10% by weight relative to the total weight of the composition.

20. The composition according to claim 1, wherein the at least one water-insoluble carboxylic acid ester is chosen from monoesters formed from an acid chosen from saturated and unsaturated, linear and branched ($C_1$–$C_{26}$) aliphatic acids and an alcohol chosen from saturated and unsaturated, linear and branched ($C_1$–$C_{26}$) aliphatic alcohols, the total number of carbon atoms in the esters being greater than or equal to 10; esters formed from an acid chosen from ($C_4$–$C_{22}$) di- and tricarboxylic acids and and alcohol chosen from ($C_1$–$C_{22}$) alcohols; and esters formed from an acid chosen from mono-, di- and tricarboxylic acids and an alcohol chosen from ($C_2$–$C_{26}$) di-, tri-, tetra- and pentahydroxy alcohols.

21. The composition according to claim 1, wherein the at least one water-insoluble carboxylic acid ester is chosen from ethyl and isopropyl palmitates, 2-ethylhexyl palmitate, 2-octyldecyl palmitate, alkyl myristates, dioctyl malate, hexyl laurate, 2-hexyldecyl laurate isononanate, isononyl isononanate, and cetyl octanoate.

22. The composition according to claim 21, wherein the alkyl myristates are chosen from isopropyl myristate, butyl myristate, cetyl myristate, 2-octyldodecyl myristate, hexyl stearate, butyl stearate, and isobutyl stearate.

23. The composition according to claim 1, wherein the at least one water-insoluble carboxylic acid ester is present in the composition in a weight content ranging from 0.001% to 10% relative to the total weight of the composition.

24. The composition according to claim 23, wherein the water-insoluble carboxylic acid ester is present in the composition in a weight content ranging from 0.005% to 5% relative to the total weight of the composition.

25. The composition according to claim 1, wherein the composition has a pH ranging from 4 to 9.

26. A method for cleansing, caring for, conditioning, or styling hair comprising applying to said hair a detergent composition comprising at least one washing base, at least one water-insoluble carboxylic acid ester and at least one amphoteric polymer comprising at least one monomeric unit chosen from (meth)acrylate and (meth)acrylamide types containing at least one fatty chain, the fatty chain containing from 8 to 30 carbon atoms
   wherein the at least one amphoteric polymer results from copolymerization
   1) of at least one monomer chosen from (meth)acrylate and (meth)acrylamide types of formula (Ia) and (Ib):

$$R_1-CH=C(R_2)-C(=O)-Z-(C_nH_{2n})-N^+(R_3)(R_4)(R_5) \quad A^- \quad \text{(Ia)}$$

$$R_1-CH=C(R_2)-C(=O)-Z-(C_nH_{2n})-N(R_3)(R_4) \quad \text{(Ib)}$$

in which:
   $R_1$ and $R_2$, which may be identical or different, are a hydrogen atom or a methyl radical; $R_3$, $R_4$ and $R_5$, which may be identical or different, are chosen from linear and branched alkyl radicals containing form 1 to 30 carbon atoms:
   Z is an NH group;
   n is an integer ranging from 2 to 5; and
   A is an anion derived from an organic or inorganic acid,
   2) of at least one monomer chosen from (meth)acrylate and (meth)acrylamide types of formula (II)

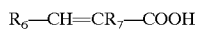  (II)

in which: $R_6$ and $R_7$, which may be identical or different, are a hydrogen atom or a methyl radical; and 3) of at least one monomer chosen from (meth)acrylate and (meth)acrylamide types of formula (III):

  (III)

in which: $R_6$ and $R_7$, which may be identical or different, are a hydrogen atom or a methyl radical: X is an oxygen atom; and $R_8$ is chosen from linear and branched alkyl radicals containing from 1 to 30 carbon atoms;

wherein at least one of the (meth)acrylate and (meth)acrylamide type monomers of formula (Ia), (Ib) or (III) comprise at least one fatty chain containing from 8 to 30 carbon atoms.

27. A process for washing and conditioning a keratin substance comprising:

applying to the substance an effective amount of a composition comprising, at least one washing base, at least one water-insoluble carboxylic acid ester and at least one amphoteric polymer comprising at least one monomeric unit chosen from (meth)acrylate and (meth)acrylamide types containing at least one fatty chain, the fatty chain containing from 8 to 30 carbon atoms, wherein the at least one amphoteric polymer results from copolymerization 1) of at least one monomer chosen from (meth)acrylate and (meth)acrylamide types of formula (Ia) and (Ib):

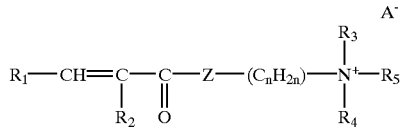  (Ia)

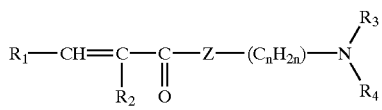  (Ib)

in which:

$R_1$ and $R_2$, which may be identical or different, are a hydrogen atom or a methyl radical; $R_3$, $R_4$ and $R_5$, which may be identical or different, are chosen from linear and branched alkyl radicals containing form 1 to 30 carbon atoms:

Z is an NH group;

n is an integer ranging from 2 to 5; and

A is an anion derived from an organic or inorganic acid, 2) of at least one monomer chosen from (meth)acrylate and (meth)acrylamide types of formula (II)

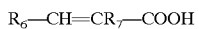  (II)

in which: $R_6$ and $R_7$, which may be identical or different, are a hydrogen atom or a methyl radical; and 3) of at least one monomer chosen from (meth)acrylate and (meth)acrylamide types of formula (III):

  (III)

in which: $R_6$ and $R_7$, which may be identical or different, are a hydrogen atom or a methyl radical: X is an oxygen atom; and $R_8$ is chosen from linear and branched alkyl radicals containing from 1 to 30 carbon atoms;

wherein at least one of the (meth)acrylate and (meth)acrylamide type monomers of formula (Ia), (Ib) or (III) comprise at least one fatty chain containing from 8 to 30 carbon atoms.

\* \* \* \* \*

UNITED STATES PATENT AND TRADEMARK OFFICE
CERTIFICATE OF CORRECTION

PATENT NO. : 6,432,908 B1  
DATED : August 13, 2002  
INVENTOR(S) : Claude Dubief et al.

It is certified that error appears in the above-identified patent and that said Letters Patent is hereby corrected as shown below:

Column 10,
Line 25, "form" should read -- from --.

Column 11,
Line 39, "dimethylaminoproply" should read -- dimethylaminopropyl --.
Line 41, "dimethylaminoproplymethacrylamide" should read
-- dimethylaminopropylmethacrylamide --.
Line 59, after "least" insert -- one --.

Column 12,
Line 7, "and and alcohol" should read -- and an alcohol --.
Line 61, "form" should read -- from --.

Column 14,
Line 13, "form" should read -- from --.

Signed and Sealed this

Eleventh Day of March, 2003

JAMES E. ROGAN
*Director of the United States Patent and Trademark Office*